United States Patent [19]
Pianetti

[11] Patent Number: 5,158,566
[45] Date of Patent: Oct. 27, 1992

[54] METAL CLIP WITH FOUR POINTS WHICH CONVERGE IN PAIRS, FOR THE SIMULTANEOUS SUTURE OF THE CUTANEOUS TISSUE AND SUBCUTANEOUS TISSUE

[76] Inventor: Francesco Pianetti, Via Turati, 22, 20013 Magenta, Italy

[21] Appl. No.: 640,814

[22] Filed: Jan. 14, 1991

[30] Foreign Application Priority Data

Jan. 15, 1990 [IT] Italy .............................. 19062 A/90

[51] Int. Cl.⁵ ........................................... A61B 17/00
[52] U.S. Cl. .................................. 606/216; 606/219; 606/221
[58] Field of Search ............... 606/213, 214, 215, 216, 606/220, 221, 219

[56] References Cited

U.S. PATENT DOCUMENTS

| | | | |
|---|---|---|---|
| 3,068,870 | 12/1962 | Levin | 606/216 |
| 4,467,805 | 4/1984 | Fukuda | 606/216 |
| 4,924,866 | 5/1990 | Yoon | 606/216 |
| 4,930,502 | 6/1990 | Chen | 606/216 |
| 4,997,439 | 3/1992 | Chen | 606/216 |
| 5,047,047 | 9/1991 | Yoon | 606/216 |

FOREIGN PATENT DOCUMENTS 1324556  3/1963  France .

Primary Examiner—Stephen C. Pellegrino
Assistant Examiner—Gary Jackson

[57] ABSTRACT

A metal clip for the simultaneous suture of the cutaneous tissue and subcutaneous tissue, consisting of two arch-shaped arms of larger radius with two points at their ends, and two arch-shaped arms of smaller radius with two points at their ends. The arms are joined together by a common segment to form a rigid system.

8 Claims, 2 Drawing Sheets

METAL CLIP WITH FOUR POINTS WHICH CONVERGE IN PAIRS, FOR THE SIMULTANEOUS SUTURE OF THE CUTANEOUS TISSUE AND SUBCUTANEOUS TISSUE

DESCRIPTION OF THE BACKGROUND ART

Metal clips with two converging points for cutis suture are known. Such clips have various drawbacks, of which the following merit particular mention:

the epidermic layer and dermic layer can undergo relative slippage both during the positioning of the clip and during the days following the operation as the patient leaves the bed;

stitches of catgut or other material reabsorbable in the subcutis have also to be applied to keep the two edges of this layer exactly mating during the days following the operation;

during the final cicatrization, introversion of the cutis surface takes place, with the formation of a permanent cutaneous groove.

SUMMARY OF THE INVENTION

The drawbacks of the known art are obviated by the metal clip for the simultaneous suture of the cutaneous tissue and subcutaneous tissue according to the present invention, which is characterised by the presence of four points converging in pairs, of which two are located at the ends of two arch-shaped arms of larger radius, and the remaining two are located at the ends of two arms of smaller radius, the arms having a common segment and the points converging towards the same vertical axis.

The points of the two smaller arms are for insertion into the epidermic and dermic tissue and the points of the larger arms are for fixing into the subcutaneous tissue.

Application of the suture clip according to the invention results in perfect mating of the edges of the epidermic layer and of the edges of the dermic layer, together with perfect confrontation of the edges of the subcutaneous layer, the cicatrization then taking place without introversion of the cutis surface.

These and further characteristics of the metal clip with four points converging in pairs for the simultaneous suture of the cutaneous tissue and subcutaneous tissue according to the present invention will be more apparent from the following detailed description. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Some preferred embodiments of said metal clip are shown in FIGS. 1 to 5, whereas

Figure 1:
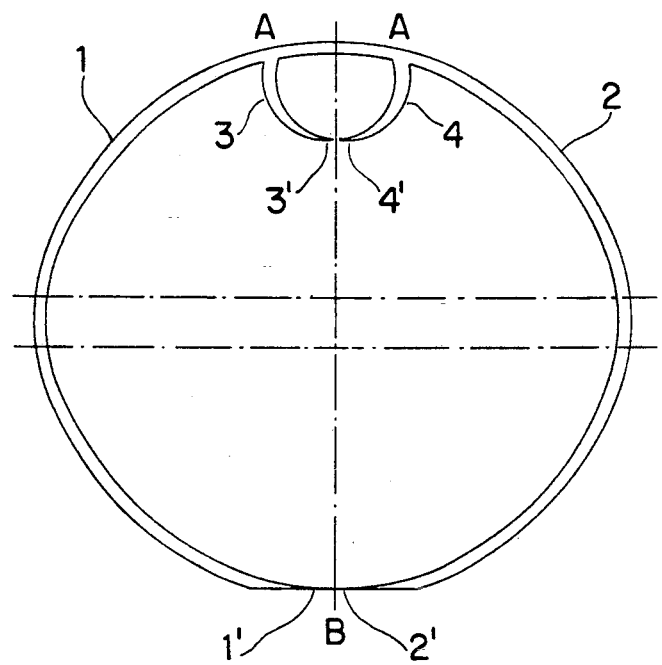
Figure 2:
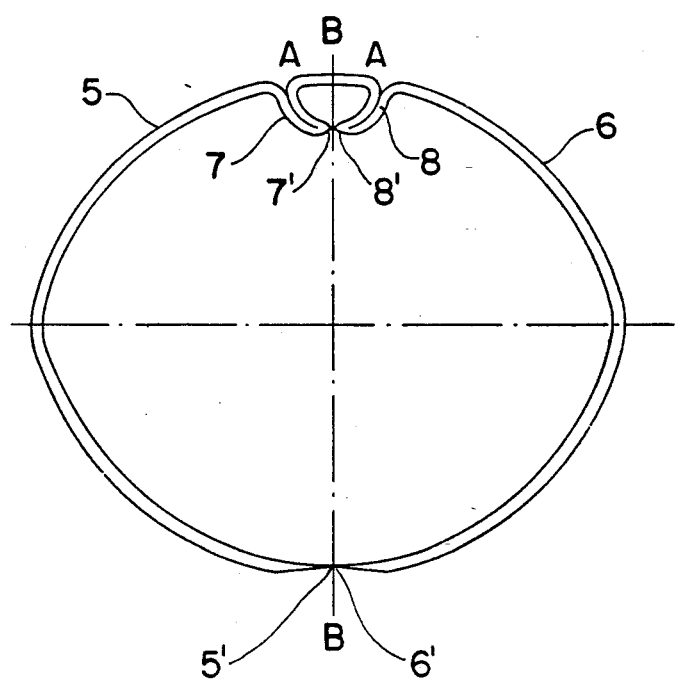
Figure 3:
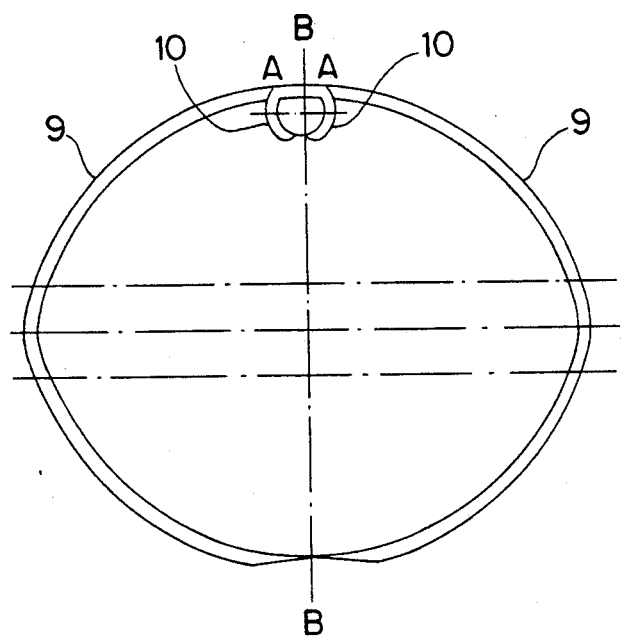
Figure 4:
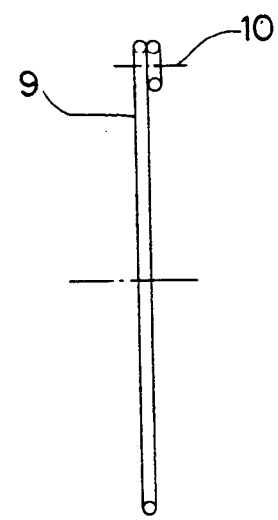
Figure 5:
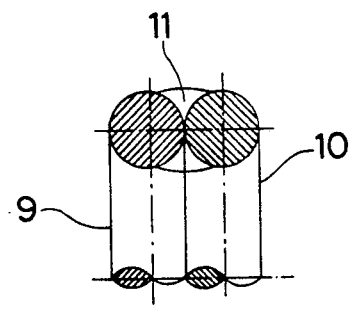
Figure 6:
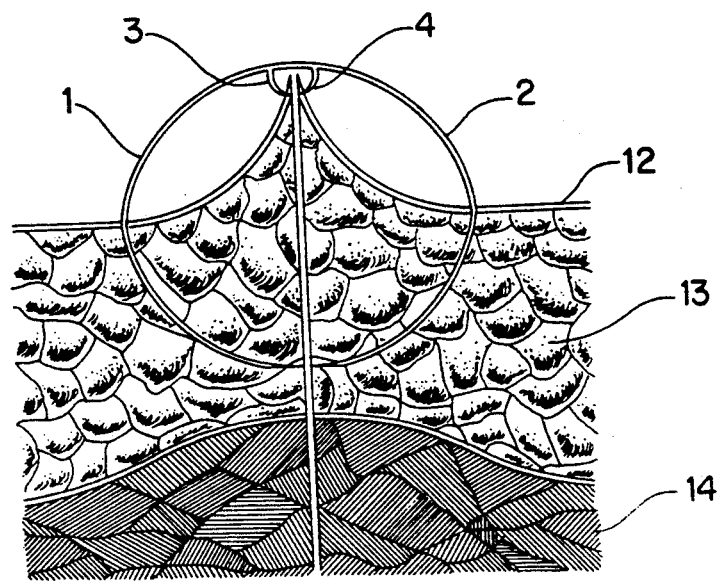
FIG. 6 shows an application of said clip.

The present invention will become more fully understood from the detailed description given herinbelow and the accompanying drawings which are given by way of illustration only, and thus are not limitative of the present invention, and wherein:

FIG. 1 shows an embodiment with the two smaller arms applied to the two larger arms to form a single system;

FIG. 2 shows an embodiment in which the two smaller arms are formed by bending back the larger arms;

FIGS. 3, 4 and 5 show an embodiment in which the two smaller arms are welded to the two larger arms along a short common segment;

FIG. 6 shows the application of the clip of FIG. 1 to the suture of a surgical wound.

DETAILED DESCRIPTION OF THE PREFERRED EMBODIMENTS

Independently of the particular embodiment, the characteristic of the suture clip according to the present invention which is common to all embodiments is that the four points which converge in pairs lie at the ends of two arch-shaped arms of larger radius and of two arms of smaller radius respectively, said arms having a common segment and said points converging towards the same vertical axis. A further common characteristic is that the two arms of larger radius are in the form of slightly acute arches to form overall an elliptical figure having its horizontal diameter greater than its vertical diameter by between 1/6 and ⅓ of the vertical diameter itself.

Using the reference symbols on the various figures, the clip shown in FIG. 1 consists of two arch-shaped arms 1 and 2 terminating in convergent points 1' and 2', and two arch-shaped arms 3 and 4 terminating in convergent points 3' and 4'. The two pairs of arms are joined together by the common segment AA, the four points converging towards the same vertical axis BB.

The arms 1 and 2 are in the geometrical form of a slightly acute arch so that the horizontal diameter is greater than the vertical diameter, to the extend that a horizontal diameter of 25 mm corresponds to a vertical diameter of 21 mm.

These dimensions can obviously vary according to the height or thickness of the cutaneous and subcutaneous tissue into which the clip is applied.

The geometrical form prevents the decubital sign of the metal wire appearing on the epidermic layer when the clip is removed. The suture clip of FIG. 1 can be produced in one piece or alternatively the two arms 3 and 4 can be welded to the arms 1 and 2 respectively.

In the embodiment of FIG. 2 the suture clip according to the invention is formed from a single continuous metal wire which is bent back to obtain the arms 7 and 8 and the arms 5 and 6, the ends of the various arms being pointed by sharpening.

A further embodiment is shown in FIGS. 3 to 5 in which two separate elements forming respectively the two arms 9 and the two arms 10 are joined together by a weld 11 along the common curvature portion AA.

In all cases, the suture clip according to the present invention consists of a wire of inert metal such as stainless steel or titanium of diameter between 4 and 7 tenths of a millimeter. An example of suture application using the clip of FIG. 1 is shown in FIG. 6 in which 12 indicates the epidermic and dermic layer, 13 indicates the subcutaneous adipose layer and 14 the muscle tissue. The points of the smaller diameter arms 3 and 4 are inserted into the dermis whereas the points of the larger diameter arms 1 and 2 are applied to the subcutaneous layer. As can be seen from this figure, suturing with the clips of the invention results in lifting of the cutaneous and subcutaneous layers, so enlarging the cut surface in the vertical direction. The clips are easily removed using a three point extractor of the type normally used for removing metal clips of the known art. The method used for their removal is also the same, with the advantage that the two exterior angles formed by the bifurcation between the two larger arches and the two smaller arches act as a guide for the two lower points of the extractor.

The use of the suture clips of the invention results in numerous advantages, including:

perfect mating of the edges of the epidermic layer and the edges of the dermic layer. These two layers cannot slip relative to each other either on the day of the operation or on the succeeding days when the patient begins to leave the bed;

there is no need to apply stitches to the subcutis because the two lower points keep the two edges of this layer properly confronting even during the days following the operation.

slippage of the dermic and subcutaneous layers is prevented both in the latero-lateral direction and in the vertical direction;

during final cicatrization there is no introversion of the cutis surface with the creation of a permanent cutaneous groove, for two reasons:

a) the lifting of the dermic and epidermic layer (FIG. 6) results in perfect mating of the surface epidermic layers with each other and of the edges of the underlying subcutaneous layer, so providing complete "restitutio ad integrum" even in the microscopic sense;

b) the cutaneous cut surface is enlarged vertically (FIG. 6), allowing a vertically more extensive cicatrix to be obtained. When this cicatrix finally contracts and consolidates it will have the same thickness as the layers which it traverses, and which is equal to the thickness these layers had on sectioning at the commencement of the operation;

finally, for the reasons given under b), the cicatrix at the cut surface does not exhibit a retracting action on the sectioning line of the dermis and epidermis, this being a further reason why the surface cutaneous groove does not appear.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A metal clip for simultaneous suture of cutaneous tissue and subcutaneous tissue, comprising two arch-shaped arms of a first radius and two arch-shaped arms of a second radius, the first radius being larger than the second radius, the arms having four points converging in pairs, two of the four points being located at ends of the two arch-shaped arms of the first radius, and the remaining two points being located at ends of the two arms of the second radius, said arms having a common segment and said points converging towards a generally vertical axis, the arms of the first radius being formed in slightly acute arches to form an overall elliptical shape having a horizontal diameter greater than a vertical diameter thereof by between 1/6 and ⅓ of the vertical diameter.

2. A metal clip as claimed in claim 1, wherein the clip is constructed in one piece.

3. The metal clip as claimed in claim 2, wherein the clip is constructed by welding the pairs of arms.

4. The metal clip as claimed in claim 1, wherein the arms of the first radius and the arms of the second radius are obtained by bending a single wire.

5. The metal clip as claimed in claim 1, wherein the two pairs of arms are joined together by a weld along a portion of common curvature thereof, each of the pair of arms being formed from an element.

6. The metal clip as claimed in claim 1, wherein the arms are made of an inert metal wire having a diameter between 4 and 7 tenths of a millimeter.

7. The metal clip as claimed in claim 6, wherein the wire is one of stainless steel and titanium.

8. The metal clip as claimed in claim 1, wherein said arms are joined together by a weld along a common segment thereof.

* * * * *